United States Patent [19]

Fischell et al.

[11] Patent Number: 4,768,507
[45] Date of Patent: Sep. 6, 1988

[54] INTRAVASCULAR STENT AND PERCUTANEOUS INSERTION CATHETER SYSTEM FOR THE DILATION OF AN ARTERIAL STENOSIS AND THE PREVENTION OF ARTERIAL RESTENOSIS

[75] Inventors: Robert E. Fischell, Silver Spring, Md.; Tim A. Fischell, Palo Alto, Calif.

[73] Assignee: MedInnovations, Inc., Dayton, Md.

[21] Appl. No.: 93,110

[22] Filed: Aug. 31, 1987

Related U.S. Application Data

[63] Continuation of Ser. No. 832,216, Feb. 14, 1986, abandoned.

[51] Int. Cl.⁴ .............................................. A61B 17/00
[52] U.S. Cl. ................................. 128/303 R; 128/341
[58] Field of Search .................... 128/303 R, 341, 343, 128/345, 334 R, 348.1; 623/1

[56] References Cited

U.S. PATENT DOCUMENTS 4,503,569 3/1985 Dotter ........................ 128/303 R X
4,553,545 11/1985 Maass et al. ........................ 128/341

Primary Examiner—Michael H. Thaler
Attorney, Agent, or Firm—Howard W. Califano

[57] ABSTRACT

This invention is in the field of percutaneous insertion catheters that are used for placing a coil spring stent into a vessel of a living body for the purposes of enhancing luminal dilation, preventing arterial restenosis and preventing vessel blockage resulting from intimal dissection following balloon and other methods of angioplasty. The stent can also be used for the maintaining patency of many different ducts or vessels within a living body.

6 Claims, 3 Drawing Sheets

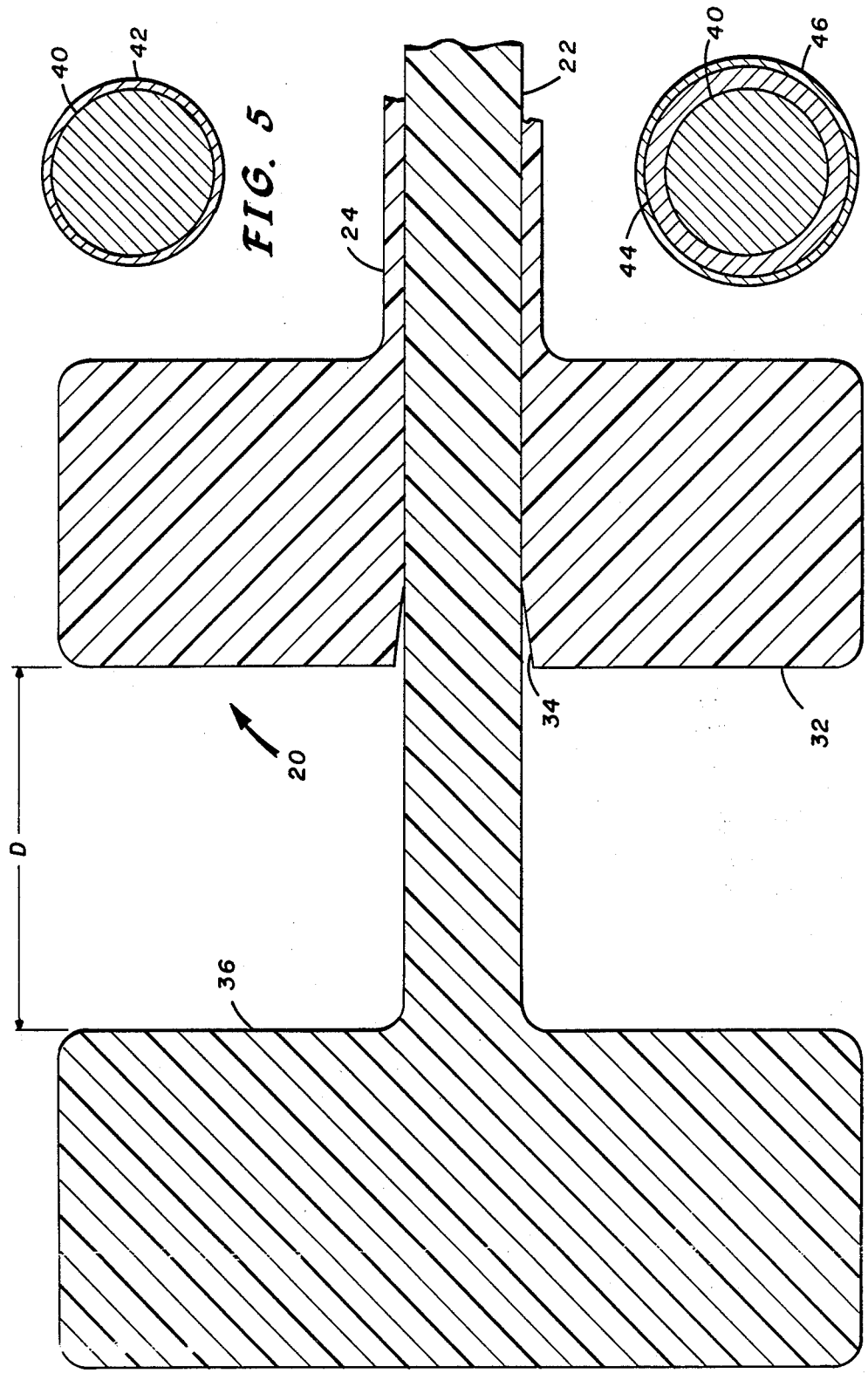

INTRAVASCULAR STENT AND PERCUTANEOUS INSERTION CATHETER SYSTEM FOR THE DILATION OF AN ARTERIAL STENOSIS AND THE PREVENTION OF ARTERIAL RESTENOSIS

This is a continuation of co-pending application Ser. No. 832,216, filed on 2-14-86, now abandoned.

BACKGROUND OF THE INVENTION

In the last decade there has been increasing use of percutaneous transluminal balloon angioplasty for the opening of stenoses of the peripheral and coronary arteries. In this procedure the uninflated balloon at the tip of the catheter is advanced into the narrowed portion of the arterial lumen. The balloon is then inflated so as to push the stenotic plaque outward thereby enlarging the luminal diameter and improving distal perfusion. The balloon is then deflated and the catheter is withdrawn from the body. Initially the blood flow at that point is typically improved to a significant degree. However, within six months, restenosis, defined as a loss of more than 50% of the initial enlargment of arterial diameter, occurs in approximately 30% of cases. It would therefore be of great value if a means could be devised to retain patency (i.e. opening) of the artery so that adequate blood flow would be maintained.

The concept of placing a coil spring intravascular stent within an artery is not new. In the September-October 1969 edition of *Investigative Radiology*, C. T. Dotter reported the insertion of 6 coil spring intravascular stents in the arteries of dogs. Three of these springs which were covered with silicone rubber occluded within 24 hours. Two out of three, bare stainless steel wire springs remained patent at 2½ years. Dotter also described a "pusher-catheter" of equal diameter with the spring outer diameter which was used to place the springs within the artery.

In more recent work, D. Maas et al in the September 1984 edition of *Radiology* described improved stainless steel coil spring intravascular stents that were implanted in 65 dogs and 5 calves. A 100% success rate was reported using bare, heat treated steel alloy springs that were torqued to a reduced diameter and inserted with a special device designed for that purpose.

Neither Dotter nor Maas at all were able to perform a percutaneous procedure for the stent insertion. Dotter describes a "pusher-catheter" that was of equal diameter to the outside diameter of the coil spring. Maas et. al. used a 7 mm diameter special insertion device that applied torque to the coil spring to reduce its diameter to 7 mm; i.e., the deployed outside diameter was greater than 7 mm. Since the largest practical outside diameter for percutaneous delivery is less than 4 mm, the device and methods used by Maas et al are not practical for percutaneous insertion.

The results of Dotter i.e. 2 of 3 patent arteries at the end of 2½ years using comparatively small (3.5 mm) diameter coil are probably not good enough for clinical applications. The results of Maas et al were very good, but these were for inside diameters greater than 7 mm.

What is really needed and not described by either Dotter or Maas et al or anyone else is a safe and simple method for percutaneous transluminal insertion of a coil spring stent whose insertion device structure allows an insertion catheter of outer diameter less than 4 mm. Another requirement of the insertion device is that it maintains the reduced diameter of the coil spring stent during insertion and allows the coil to expand to a diameter greater than the diameter of the arterial lumen after removal of the insertion catheter.

To make the intravascular stent (IS) safe for human use even in small diameter coronary arteries, it is necessary for the spring material to be biocompatible and non-thrombogenic. The greatest success by Dotter and Maas et al was with bare metal coil springs. However, no investigation to date has described use of these stents in either human subjects or in animal coronary arteries. Furthermore, Dotter quotes an article which states that "It appears that success or failure of an arterial substitute in dogs bears no direct relationship to the results one will obtain when a similar substitute is used clinically for the peripheral arteries". Hence one must be concerned with the human biocompatability of the material used for the IS.

Many articles such as "ULTI Carbon Goretex: A New Vascular Graft" by R. Debski et al in the May-June 1983 edition of *Current Surgery* describe the superior non-thrombogenic characteristics of ultra low-temperature isotropic (ULTI) carbon as such a blood compatible material. The use of carbon as a blood compatible material for humans is well known among those skilled in the art of vascular grafts and prosthetic heart valves. However, no investigator of IS devices has ever described the use of carbon coated coil springs or carbon coated polytetrafluoroethylene (PTFE) covered coil springs to solve the problem of thrombosis of small diameter IS devices in humans.

It should be noted that nothing in the prior art describes the use of a coil spring stent for the prevention of arterial blockage due to intimal dissection (tearing away of the intima layer) following balloon angioplasty. There is appproximately a 30% incidence of radiologically detectable intimal dissection following routine percutaneous transluminal coronary angioplasty (PTCA). In many of these cases this is not a problem. Vessel wall healing and remodeling typically restores a smooth luminal contour with good vessel patency within several weeks following the angioplasty. In a small but significant subset of these patients, the intimal dissection may be severe, resulting in a high risk of vessel closure within 24 hours following PTCA. These patients will typically sustain some degree of myocardial infarction despite further aggressive attempts at revascularization, including coronary artery bypass surgery.

SUMMARY OF THE INVENTION

Thus it is an objective of the present invention to utilize a coil spring intravascular stent (IS) for the prevention of arterial restenosis.

A second objective of the invention is to utilize an IS to further enlarge the luminal diameter after successful percutaneous transluminal angioplasty.

Another objective is to provide a percutaneous transluminal catheter means for placing the IS at the appropriate place within the artery.

Still another objective is to describe a method for percutaneous insertion of intravascular stents.

Still another objective is to provide a means and method for preventing arterial blockage due to intimal dissection following balloon or other types of angioplasty.

BRIEF DESCRIPTION OF THE DRAWINGS

FIG. 4 is a cross-sectional view of the proximal end of the insertion catheter.

FIG. 5 is a cross-sectional view of a wire coated with ULTI carbon.

FIG. 6 is a cross-sectional view of a wire enclosed by PTFE and coated with ULTI carbon.

DETAILED DESCRIPTION OF THE INVENTION

Figure 1A:
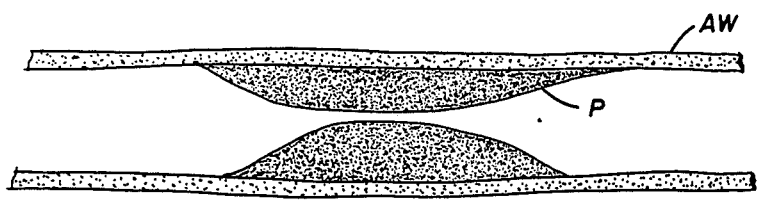
FIGS. 1A, 1B and 1C are cross-sectional views showing respectively the shape of the plaque within an arterial wall, (A) before balloon dilation, (B) immediately after balloon dilation, and (C) at several months after dilation.
Figure 1B:
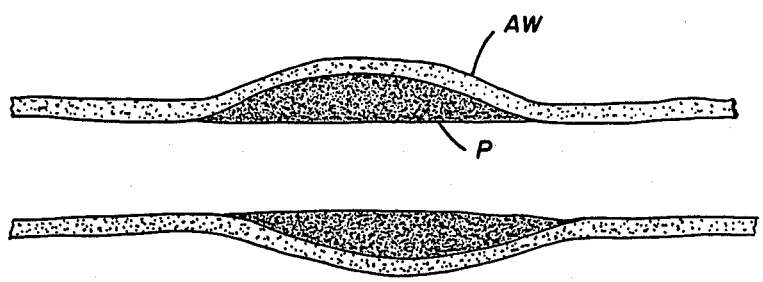
Figure 1C:
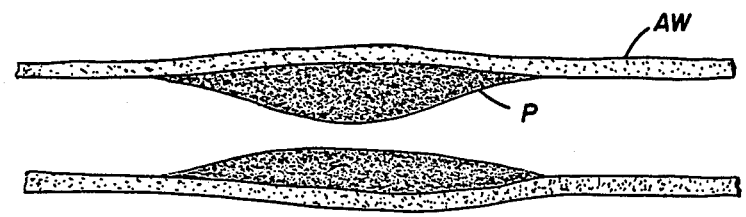

FIGS. 1A, 1B and 1C are cross-sectional views of an arterial wall AW surrounding a plaque P which forms an arterial stenosis or narrowing. It is well known in the art to utilize percutaneous transluminal balloon angioplasty to dilate the stenosis of FIG. 1A by expanding a balloon that is placed within the narrowed lumen. The result immediately after balloon dilation is shown in FIG. 1B. However, in approximately 30% of all balloon procedures, there is a restenosis of the artery as illustrated in FIG. 1C.

Figure 2:
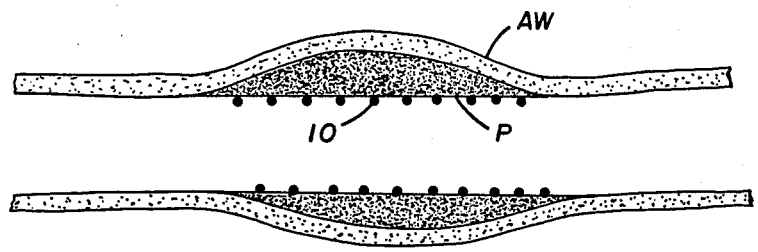
FIG. 2 is a cross-sectional view of an IS in the form of a coil spring placed in a position to prevent restenosis and/or provide additional dilation of the plaque.

If however, a coil spring intravascular stent (IS) 10 is placed at the dilation site immediately after balloon dilation in a position as shown in FIG. 2, the resistance of the IS 10 to deformation by inwardly directed radial pressure can preclude restenosis of the artery. Furthermore, if the constrained diameter of that IS 10 as shown in FIG. 2 is less then the free diameter of the coil spring IS 10, then additional dilation may occur following the insertion of the IS 10. Furthermore, if the intima layer was torn (i.e. dissected) during balloon dilation, the IS 10 can hold that intima layer in place and prevent subsequent blockage of the artery which can result from the effect of blood flow causing the torn intima to come off the wall of the dilated stenosis.

Figure 3:
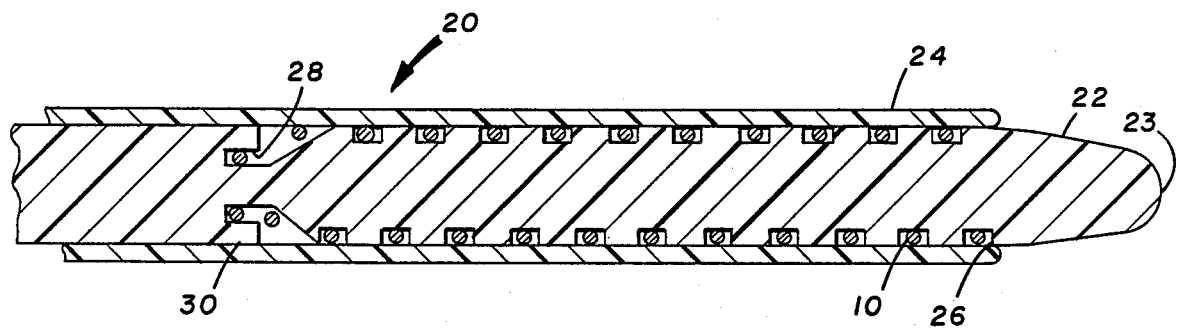
FIG. 3 is a cross-sectional view of the distal end of an insertion catheter for inserting the IS.

FIG. 3 shows the distal end of the insertion catheter 20 which consists of an inner core 22 and an outer cylinder 24. The core 22 has a rounded and tapered front end 23 and spiral grooves 26 into which the coil spring IS 10 is placed. The core 22 has a back groove 28 which contains the most proximal coil of the coil spring IS 10 which is prevented from springing radially outward by the flange 30.

FIG. 4 is a cross-sectional view of the proximal end of the insertion catheter 20. A cylindrically shaped cylinder handle 32 is molded onto the outer cylinder 24. Similarly, a cylindrically shaped core handle 36 is molded onto the core 22. A conically shaped interior surface 34 of the cylinder handle 32 is used to help guide the cylinder handle 32 over the IS 10 as it is mounted on the distal end of the insertion catheter 20. The distance D in FIG. 4 is initially set to be slightly greater than the length of the IS 10 at the distal end of the insertion catheter 20.

The spring IS 10 is loaded onto the distal end of the core in the following manner:

1. A pair of pliers is used to hold the most distal portion of the IS 10 into the most distal spiral groove 26 of the inner core 22.
2. The spring IS 10 is then pulled and twisted applying torque to its most proximal end so that the spring IS 10 is forced into the spiral grooves 26.
3. A pliers wide enough to hold all turns of the IS 10 in place except the most proximal turn and the most distal turn is then applied at the center of the IS 10 to hold it in the spiral grooves 26.
4. A needle nose pliers is then used to force the most proximal turn of the IS 10 into the core groove 28.
5. The conical interior surface 34 of the cylindrical handle 32 is then fed over the most distal turn of the IS 10 as it sits in the most distal groove 26 of the core 22.
6. As the handle 32 is moved in the proximal direction, the broad pliers holding the central portion of the IS 10 in place is simultaneously moved in the proximal direction until the entire IS 10 is covered by the interior surface of the handle 32 and the outer cylinder 24.
7. The handle 32 is then pulled in a proximal direction until the distal end of the cylinder 24 lies just over the last turn of the IS 10 which occurs when the cylinder handle 32 and the core handle 36 are separated by a distance D as shown in FIG. 4.

In this manner, a coil spring IS 10 whose unrestrained (i.e. free) diameter can be between 1.1 to 5.0 times larger than its diameter when stored on the core 22 can be placed at the distal end of the insertion catheter 20.

Deployment of the spring IS 10 within a recently dilated occlusion is accomplished in the following steps:

1. By conventional means, a guiding catheter (not shown) is placed percutaneously into the femoral artery and its distal end is advanced to the site where the IS 10 is to be released.
2. Under fluoroscopic control, the insertion catheter 20 is advanced through the guiding catheter until the center of the IS 10 is positioned at the center of the recently dilated stenosis.
3. While holding the core handle 36 firmly against the body so that it does not move, the outer cylinder handle 32 is move proximally so as to decrease to zero the distance D of FIG. 4.
4. All turns of the IS 10 except the most proximal turn are then expanded outward to engage the interior surface of the recently dilated stenosis.
5. The core 22 and the outer cylinder 24 are then pulled out of the body together which leaves the coil spring IS 10 in its desired place in the artery.

An angioplasty balloon could then be expanded within the IS 10 so as to more firmly imbed the spring into the stenotic plaque. The balloon and guiding catheters would of course be removed from the body after they were used for their intended purposes.

The coil spring used in this manner would:

1. Prevent restenosis of the occlusion.
2. Increase the lumen diameter by constantly applying an outward radial force to the plaque, and
3. Hold in place any intima layer torn from the stenosis during balloon dilation which might otherwise tend to block blood flow in that artery.

The materials of the core 22, core handle 36, outer cylinder 24 and outer cylinder handle 32 might be PVC or some other comparatively strong plastic. The IS 10 might be fabricated from a stainless spring steel or an alloy of titanium such as Ti-6A1-4V. The outside diameter of the unrestrained coil spring IS 10 might vary from 2 to 12 mm depending on the lumen diameter into which it is implanted. The wire diameter might be between 0.1 and 0.5 mm. The outer diameter of the outer cylinder 24 would be less than 4 mm. The length of the IS 10 would be between 5 and 25 mm depending upon the length of the dilated stenosis into which it would be placed.

Decreased thrombogenicity can be achieved by coating the outside of the coil with a non-thrombogenic material such as ULTI carbon. An enlarged cross section of such a wire is shown in FIG. 4. The metallic core is shown as 40 and the coating is shown as 42. Coating thickness might be as thin as 0.01 mm or as thick as 0.1 mm.

FIG. 5 shows another enlarged cross section of the wire of the IS 10 in which the metallic core 40 is first covered by a plastic layer 44 such as PTFE and then coated with a nonthrombogenic coating 46 such as ULTI carbon. The plastic coating would typically be between 0.05 and 0.5 mm and the non-thrombogenic coating might have a thickness between 0.01 and 0.5 mm.

Although this intravascular stent might find its greatest application as a means to enhance balloon angioplasty in humans it could also be used to successfully provide permanent dilation and patency of other ducts and vessels within a living human or animal body. For example, this coil spring intravascular stent 10 could also be used to maintain long term patency of ureters or fallopian tubes. In every use, the fact that wire diameter would be typically 1/10 the coil spring pitch length i.e., only 10% of the lumen interior surface is actually in contact with a foreign material. Therefore, normal body cells could grow over the coils of such springs. Thus, the normal characteristics of the interior lining of such ducts or vessels would be only minimally compromised.

Various other modifications, adaptations, and alternative designs are, of course, possible in light of the above teachings. Therefore, it should be understood at this time that within the scope of the appended claims, the invention may be practiced otherwise than as specifically described herein.

What is claimed is:

1. A stent insertion apparatus comprising: an inner core member having distal and proximal ends and a spiral groove formed on its outer surface;
    a hollow outer sheath cylinder having distal and proximal ends and having an inner surface slidably mounted around said inner core member and movable relative to said inner core member from a first position covering said spiral groove of said inner core member to a second position exposing the spiral groove of said inner core member, wherein cooperation of the spiral groove of said inner core member with the inner surface of said hollow sheathing cylinder forms a spiral cavity adapted to contain a coil stent when said sheathing cylinder is in said first position; and,
    a coil stent held in a radially compressed state within said spiral cavity by exerting a radial outward force on said sheathing cylinder when said sheathing cylinder is in its first position, and is released from said spiral cavity and expandable by its intrinsic mechanical properties to a larger diameter when said sheathing is in its second position without the requirement of relative axial rotation between the inner core member and the outer sheathing cylinder.

2. The apparatus of claim 1, wherein said inner core member further comprises a flange means, adapted to frictionally engage the proximal end of said coil stent.

3. The apparatus of claim 2, wherein said flange means comprises:
    a back groove cut into the surface of said inner core member and adapted to contain the proximal end of said coil stent; and,
    a flange located adjacent to said back groove and adapted to prevent radial movement of said coil stent which is frictionally engaged.

4. The apparatus of claim 1, wherein said inner core member comprises a rounded and tapered distal end.

5. The apparatus of claim 1, further comprising a control means of moving the distal end of said sheathing cylinder from said first position to said second position relative to the distal end of said inner core member and deploying said coil stent without the requirement of axial rotation of the outer sheathing cylinder relative to the inner core member.

6. The apparatus of claim 5, wherein the proximal end of said sheathing cylinder and said inner core member extend external to said living body, and wherein said control means comprises a first handle operably coupled to a proximal portion of said sheathing cylinder, and a second handle operably coupled to a proximal portion of said inner core member, wherein movement of said first handle toward said second handle causes movement of the distal ends of said sheathing cylinder from said first position to said second position relative to said inner core member so as to release said coil stent.

* * * * *